United States Patent [19]

Rasmussen

[11] 4,239,768

[45] Dec. 16, 1980

[54] METHOD FOR RELIEVING IRRITABLE BOWEL SYNDROME SYMPTOMS

[75] Inventor: Chris R. Rasmussen, Ambler, Pa.

[73] Assignee: McNeilab, Inc., Fort Washington, Pa.

[21] Appl. No.: 972,580

[22] Filed: Dec. 22, 1978

[51] Int. Cl.$^3$ .......................................... A61K 31/415
[52] U.S. Cl. ................................................ 424/273 R
[58] Field of Search .................................... 424/273 R

[56] References Cited

U.S. PATENT DOCUMENTS

| | | | |
|---|---|---|---|
| 3,168,520 | 2/1965 | Kleeman et al. | 544/332 |
| 4,025,517 | 5/1977 | Rasmussen | 424/273 |
| 4,058,557 | 11/1977 | Douglas et al. | 424/273 X |

*Primary Examiner*—Frederick E. Waddell

[57] ABSTRACT

A method for alleviating functional intestinal disorders and for treating the discomfort associated therewith and compositions therefor.

6 Claims, No Drawings

METHOD FOR RELIEVING IRRITABLE BOWEL SYNDROME SYMPTOMS

FIELD OF INVENTION

This invention relates to methods for relieving intestinal disorders employing N-aryl-N'-(2-imidazolidinylidene) urea compositions.

BACKGROUND OF THE INVENTION

Irritable bowel syndrome is a functional disorder characterized primarily by abdominal pain, but also by diarrhea and constipation and like symptoms. It is believed that the pain associated with this syndrome is due to excessive sensitivity to distention of the bowel caused either by intestinal gas and/or fecal material. Treatments which would provide relief from the discomforts associated with such symptoms and/or the disorder which produce such symptoms are highly desirable.

PRIOR ART

Certain imidazolidine ureas are known in the art. Thus, in U.S. Pat. No. 3,168,520 imidazolidine ureas and hexahydropyrimidine ureas are taught. These compounds are taught to be useful as dye stabilizers. The patent specifically teaches 2-phenylcarbiliminoimidazolidine which is N-(2-imidazolidinylidene)-N'-phenylurea. There is no teaching or suggestion in the patent however for the use of imidazolidineureas and heaxhydropyrimidineureas as active ingredients in pharmaceutical compositions.

Some urea compounds have been disclosed to have certain pharmacological properties. Thus, U.S. Pat. No. 4,060,635 discloses amidinoureas. These compounds have an aryl group on one urea nitrogen and a substituted amidino group on the other urea nitrogen. U.S. Pat. No. 3,539,616 and No. 3,784,582 teach amidinoureas in which one urea nirogen is substituted with an aryl group and the other nitrogen is substituted with an unsubstituted amidino group. U.S. Pat. No. 4,058,557, also directed to amidinoureas but more remote, teaches compound in which one of the amidino nitrogens necessarily is attached to an oxygen. None of the patents teach or suggest the substitution of an imidazolidino group on a urea nitrogen.

A recent publication, G. H. Douglas et al., Arz. Forsch/Drug Res. 28(II), 1480 (1978) discloses the results of many aryl substituted amidinoureas screened for antimotility and antisecretory activity. N-(2,6-Dimethylphenyl)-N'-(2-imidazolidinylidene)urea and N-(2,6-dimethylphenyl)-N'-(1-methyl-2-imidazolidinylidene)urea are among the compounds tested. The article does not teach the compounds to have useful antimotility activity.

DESCRIPTION OF THE INVENTION

This invention is concerned with a method for treating functional intestinal disorders and for relieving pain discomfort and other symptoms associated with irritable bowel by administering to such subjects a composition comprising a N-aryl-N'-(2-imidazolidinylidene)urea compound of the formula

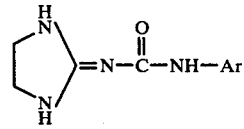

or a pharmaceutically acceptable acid addition salt thereof. It also embraces a method for inhibiting diarrhea and treating intestinal disorders wherein the foregoing urea compound is in admixture with a pharmaceutically acceptable carrier.

In the foregoing and subsequent formulas, Ar is phenyl substituted at least in the 2 and 6 positions with substituents independently selected from radicals characterized by the presence of halogen or of a carbon-containing group of from 1 to 2 carbon atoms which is optionally attached to the phenyl through a non-basic hetero atom. Representative substituents are halo, such as chloro, bromo and fluoro; lower alkyl such as methyl and ethyl; lower alkoxy, such as methoxy and ethoxy; and trifluoromethyl. In the most preferred compounds, Ar may be represented by

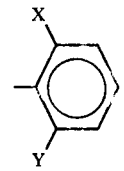

wherein X and Y are selected from methyl, ethyl, chloro and bromo.

The activities of the above compounds reside in the urea base so that useful acid addition salts may be from various acids provided only that the acids be pharmaceutically acceptable. Representative acid salts include hydrochloride, hydrobromide, hydroiodide, phosphate, sulfate, p-toluenesulfonate, benzensulfonate, malate, tartrate, fumarate, citrate, pamoate, maleate, malonate, succinate, oxalate methosulfate, methanesulfonate, 2-napsylate and the like.

The pharmacologically useful N-aryl-N'-(2-imidazolidinylidene)urea compounds are prepared by subtantially two methods. The most generally useful method is by the reaction of an appropriate 2-iminoimidazoline (II) with an aryl isocyanate (III) according to the following equation:

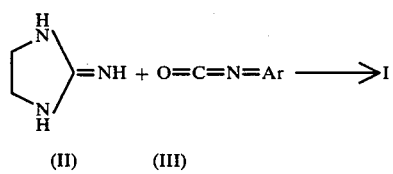

The 2-iminoimidazoline starting materials conveniently may be prepared (according to art methods and as subsequently described) and stored as an acid addition salt

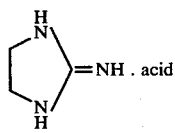

(IIa)

Thus, the initial step is usually the conversion of the acid addition salt to the free base. This may be carried out by thoroughly stirring a solution or suspension in tetrahydrofuran of the acid addition salt with two molar equivalents of 50 percent aqueous sodium hydroxide, followed by the addition of anhydrous sodium sulfate to remove excess water. The thus obtained biphasic mixture is contacted with an appropriate aryl isocyanate to produce the desired N-aryl-N'-imidazolidinylideneurea compound.

In a preferred method for carrying out the reaction between the aryl isocyanate and the 2-iminoimidazolidine, a solution of aryl isocyanate in tetrahydrofuran is added portionwise with stirring to the biphasic mixture at temperatures in the range of about 20° to 30° C. and the mixture stirred for from a few hours to overnight. The N-aryl-N'-imidazolidinylideneurea compound thus obtained is recovered, converted to an acid addition salt form, if desired, and purified employing conventional procedures.

The free base may be generated by another procedure in which a solution of 2-iminoimidazolidine acid addition salt is brought into contact with a suspension of lithium hydride, preferably, in the same solvent, in an inert atmosphere. Suitable solvents include dry dimethylformamide, dimethylsulfoxide, tetrahydrofuran, and the like. The temperature for addition is generally in the range of 0° to 30° C. An inert atmosphere is conveniently provided by use of nitrogen or argon.

In a preferred method for carrying out the reaction, a solution of 2-iminoimidazolidine acid addition salt is added dropwise with stirring to a cooled suspension of lithium hydride in a dry solvent under nitrogen atmosphere while maintaining temperatures in the 0°-5° C. range. Stirring is continued after the completion of the addition while the mixture is gradually allowed to warm to room temperature to obtain the free base.

The reaction between 2-iminoimidazolidine and aryl isocyanate may be carried out by adding a solution of an aryl isocyanate, dropwise with stirring and cooling, to the reaction mixture containing the free base in an inert atmosphere, the resulting mixture stirred while gradually warming to ambient temperature and the stirring continued for several hours or longer to obtain the desired N-aryl-N'-(2-iminoiidazolidine)urea product which may be isolated and purified by conventional procedures.

The salt may be converted to the free-base. If another salt is desired, the free base is caused to react with another acid to form a desired acid addition salt. Conventional procedures may be employed for these conversions. Thus, for example, a representative convenient procedure for obtaining the free base from the salt is dissolving the acid addition salt in a minimal amount of lower alkanol solvent such as methanol or ethanol, warming with an organic base such as triethylamine and the like, and cooling to obtain the free-base product as a crystalline solid. Similarly, a representative convenient procedure for converting the free base to an acid addition salt is mixing the base with an alcoholic solution of an acid corresponding to the addition salt desired and cooling to obtain the acid addition salt.

The N-aryl-N'-(2-imidazolidinylidene)urea compounds have been found to provide relief from the discomfort associated with functional intestinal disorders spoken of as the irritable bowel syndrome. The disorder is characterized by abdominal pain, diarrhea, constipation and like symptoms caused by excessive sensitivity to distension of the bowel by the presence of intestinal gas and/or fecal material. The extent to which a compound is effective in providing relief may be determined by a test in which a glass bead is inserted into the rectum and the lapse of time between insertion and expulsion of the bead determined. Compounds which are effective in decreasing the sensitivity to distension of th colonic wall delays the expulsion of the bead.

The test is carried out with male albino mice of 18–25 grams body weight using groups of five mice for each compound dose tested. The initial screen dose selected for all compounds is 50 milligrams per kilogram of body weight (mg/kg) administered orally in a volume of 0.1 milliliter per 10 grams of body weight. The control groups receive the vehicle, 0.5 percent methocel, used for both oral and intraperitoneal administration. The mice are fasted one hour before testing and the test drugs are given one hour prior to glass bead insertion.

At the end of the pretreatment time, the mouse is picked up and held firmly in one hand with his abdomen facing the technician. The glass bead of 3 millimeters in diameter is positioned at the rectum and using a pinching action with a thumb and forefinger, the bead is pushed into the rectum. Then using a glass rod of 3 millimeters in diameter which has been lubricated with 0.5 percent methocel to facilitate insertion, the glass bead is pushed up into the rectum a distance of 2 centimeters using a slow gentle turning motion. The mice are timed as a group using the last mouse inserted as zero time and the number of beads expelled in a group at different timed intervals are recorded. The groups are based on timed intervals of 0 to 5 minutes, 5 to 10 minutes, 10 to 20 minutes, 20 to 40 minutes and greater than 40 minutes. They are given the activity index values of 0, 1, 2, 3 and 4, respectively. Mice who have not expelled their beads by the 40-minute cutoff time are examined for perforations. Those mice whose colons are perforated are eliminated from the group. The sum of the values divided by the number of mice or beads is termed the activity index for the drug tested. The $ED_{50}$ is determined by regression lines using the method of least squares. The $ED_{50}$ is arbitrarily assigned as that dose causing an activity index of 2.

The results of this test employing intraperitoneal and oral administration of N-aryl-N'-(2-imidazolidinylidene)urea compounds are shown in Table I.

TABLE I

COMPOUND

| Ar | HX | $ED_{50}$ (mg/kg) Intraperitoneal | Per Os |
|---|---|---|---|
| 2,6-diCl-φ | HCl | 7 | 13.7 |
| 2,6-di(CH$_3$)-φ | HCl . ½ H$_2$O | 12 | 16 |

TABLE I-continued

COMPOUND $$\text{\begin{tabular}{c}H\\N\end{tabular}} \!\!\!\diagdown\!\!\! \text{\begin{tabular}{c} \\ \\N\\H\end{tabular}} \!\!=\!\! N\!-\!\overset{\overset{O}{\|}}{C}\!-\!NH\!-\!Ar$$

| | | ED$_{50}$ (mg/kg) | |
|---|---|---|---|
| Ar | HX | Intraperitoneal | Per Os |
| 2-Cl,6-CH$_3$-φ | HCl | 8 | 35 |
| 2,6-diBr-φ | HCl | 9 | 38 |
| 2-C$_2$H$_5$, 6-CH$_3$-φ | ⅔ fumarate | 43 | 121 |

The foregoing results illustrate the beneficial effect of N-aryl-N'-(2-imidazolidinylidene)urea compounds in decreasing abnormal sensitivity to distention of bowel. These properties are utilized in the methods and compositions of the present invention.

The process of the present invention, namely, a method for alleviating functional intestinal disorders and for treating the discomforts associated therewith comprises administering to subjects in need of treatment, a therapeutically effective amount of a N-aryl-N'-(2-imidazolidinylidene)urea compound of Formula I or its pharmaceutically acceptable salt as active agent. The active agents may be administered with or without carrier in the amounts hereinafter set forth. A preferred method of administration is by use of pharmaceutical compositions in unit dosage form as described below.

The operable ranges for carrying out the process is the administration, orally or parenterally, of from about 10 milligrams to about 500 milligrams of a N-aryl-N'-(2-imidazolidinylidene)urea compound in dosage unit form. While the therapeutic method is most useful for human subjects, it may also be employed for other mammals. Operable amounts are generally within the range of from about 0.50 to 50 mg/kg, preferably at least 3 mg/kg of body weight.

The outstanding properties are most effectively utilized by use of the pharmaceutical compositions of the present invention. The pharmaceutical compositions comprising a N-aryl-N'-(2-imidazolidinylidene)urea compound or acid addition salt thereof, as the active ingredient, may be prepared by intimately mixing the urea compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonsful, tablespoonsful and the like, and segregated multiples thereof. A dosage unit generally will contain from about 10 to about 500 mg of the N-aryl-N'-(2-imidazolidinylidene)urea compounds.

The following examples illustrate the preparation of the N-aryl-N'-(2-imidazolidinylidene)urea compounds and the pharmaceutical compositions suitable in the practice of the invention but are not to be construed as limiting:

STARTING MATERIAL

The 2-imidazolidine starting material of Formula II may be prepared by literature described methods or by the following representative preparation of the hydroiodide addition salt:

213 grams (1.5 moles) of methyl iodide is added with stirring over one hour to a suspension of 153.24 grams (1.5 moles) of ethylenethiourea in 300 milliliters of methanol. Stirring is continued for about an additional hour to complete the formation of S-methyl ethylenethiourea. Anhydrous ammonia then is added thereto whereupon a reaction takes place with the formation of 2-iminoimidazolidine hydroiodide and methylmercaptan by-product. The stirring and intermittent addition of ammonia is continued for a total of about 26 hours. The mixture is concentrated with concomitant addition of isopropanol to replace the vaporized methanol, and then cooled and ether added thereto to produce 2-iminoimidazoline hydroiodide as a crystalline solid which after recrystallization from methanol/tert.-butanol has a melting point of 152°–154° C.

Anal. Calcd. for C$_3$H$_7$N$_3$.HI; C, 16.92; H, 3.79
Found: C, 16.85; H, 3.82.

EXAMPLE I

N-(2,6-Dichlorophenyl)-N'-(2-imidazolidinylidene)urea Hydrochloride

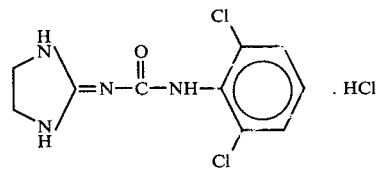

To a stirred suspension of 2.13 grams (0.01 mole) of 2-iminoimidazolidine hydroiodide in 50 milliliters of dry dimethylformamide under an atmosphere of nitrogen is added 0.8 gram (0.01 mole) of aqueous 50 percent sodium hydroxide to produce free 2-iminoimidazolidine base and sodium iodide. Thereafter, 1 gram of anhydrous sodium sulfate is added and the stirring continued for another one-half hour. To the mixture then is added dropwise over a 2.5 hour period, a solution of 0.94 gram (0.005 mole) of 2,6-dichlorophenyl isocyanate in 20 milliliters of tetrahydrofuran and the mixture allowed to stir overnight at room temperature to obtain a N-(2,6-dichlorophenyl)-N'-(2-imidazolidinylidene)urea product. The sodium salts are removed by filtration and the filtrate concentrated on a water bath under reduced pressure to obtain a pale yellow oil. The latter is dissolved in methylene chloride, and the methylene chloride solution first washed with saturated brine, dried over anhydrous potassium carbonate and treated with hydrogen chloride until pH<3 is reached. The solvent and excess hydrogen chloride are removed in vacuo and the residue recrystallized from methanol/ether to obtain purified N-(2,6-dichlorophenyl)-N'-(2-imidazolidinylidene)urea hydrochloride, m.p. 210°-212° C., which decomposes to a solid melting at 239° C.

EXAMPLE II

N-(2-Chloro-6-methylphenyl)-N'-(2-imidazolidinylidene)urea and Hydrochloride

A solution of 10.65 grams (0.05 mole) of 2-iminoimidazolidine hydroiodide in dimethylformamide is added dropwise with stirring over a 15 minute period to a cooled to 5° C. suspension of 397.5 milligrams (0.05 mole) of lithium hydride in 50 milliliters of dry dimethylformamide under nitrogen whereupon hydrogen evolution is observed. While stirring is continued, the mixture is allowed to gradually warm to room temperature. Thereafter, the reaction mixture is cooled to 0°-5° C. and a solution of 5.0 grams (0.03 mole) of 2-chloro-6-methylphenyl isocyanate in 25 milliliters of dry dimethylformamide is added dropwise over a two hour period. After completion of the addition, the mixture is allowed to warm gradually to room temperature while the stirring under nitrogen atmosphere is continued overnight to obtain the desired N-(2-chloro-6-methylphenyl)-N'-(2-imidazolidinylidene)urea product which remains in solution. The product is recovered from the reaction mixture by (a) adding the mixture to 300 milliliters of ice water with stirring, (b) lowering the pH below 2 with aqueous 10 percent hydrochloric acid to precipitate acid insoluble material (c) filtering, (d) basifying the filtrate to pH 8-9 with solid potassium carbonate, and (e) saturating the solution with solid sodium chloride to precipitate the desired N-(2-chloro-6-methylphenyl)-N'-(2-imidazolidinylidene)urea free base as a white solid. The product after washing thoroughly with water has a melting point of 169°-171° C.

The product urea base is dissolved in 30 milliliters of methanol, and methanolic hydrogen chloride added thereto to a pH below 3. Ether is then added whereupon a N-(2-chloro-6-methylphenyl)-N'-(2-imidazolidinylidene)urea hydrochloride product precipitates. The latter is recovered and recrystallized successively from 2-propanol and methanol-ether to obtain a purified product, m.p. 209°-211°, which decomposes to a solid melting at 270° C. (dec.)

Anal. Calcd. for $C_{11}H_{13}ClN_4O \cdot HCl$: C, 45.69; H, 4.88; N, 19.37. Found: C, 45.59; H, 4.93; N, 19.35.

EXAMPLE III

N-(2-Ethyl-6-methylphenyl)-N'-(2-imidazolidinylidene)urea. Fumarate (3:2)

In a manner similar to that previously described, 15.55 grams (0.073 mole) of 2-iminoimidazoline hydroiodide is added dropwise to a dry cooled suspension of 596 milligrams (0.075 mole) of lithium hydride in 30 milliliters of dimethylformamide under an atmosphere of nitrogen. After completion of the addition, the mixture is allowed to warm to room temperature to complete the reaction. Thereafter the mixture is again cooled, a solution of 8.1 grams (0.05 mole) of 2-ethyl-6-methylphenyl isocyanate in 25 milliliters of dry dimethylformamide is added dropwise over a two hour period and thereafter the resulting mixture is stirred overnight while the temperature is allowed to rise to ambient temperatures to obtain a N-(2-ethyl-6-methylphenyl-N'-(2-imidazolidinylidene)urea product. The base product is recovered by procedures similar to that previously described and after recrystallization from methanol-water, a purified base product, m.p. 185°-187° C. is obtained.

A solution of 4.32 grams (0.0175 mole) of the base product thus obtained in 35 milliliters of hot isopropanol is mixed with a solution of 2.04 grams (0.0175 mole) of fumaric acid in 35 milliliters of hot isopropanol and the resulting solution is allowed to cool whereupon a N-(2-ethyl-6-methylphenyl)-N'-(2-imidazolidinylidene)urea fumarate addition salt product crystallizes. The salt product after washing first with isopropanol and thereafter with ether mlts at 180° C. (dec.). Successive recrystallizations from methanol isopropanol, methanol/ether, and methanol does not produce a salt of reproducibly sharp melting point. Elemental analysis indicates the salt to be formed from three moles of base and two moles of fumaric acid.

Anal. Calcd. for $(C_{13}H_{18}N_4O)_3 \cdot (C_4H_4O_4)_2$: C, 58.13; H, 6.44; N, 17.31. Found: C, 58.03; H, 6.57; N, 17.59.

EXAMPLE IV

N-(2,6-Dibromophenyl)-N'-(2-imidazolidinylidene)urea and Hydrochloride

In a manner similar to that described in Examples II and III, a solution of 12.0 grams (0.0563 mole) of 2-iminoimidazolidine hydroiodide in 50 milliliters of dry dimethylformamide is added dropwise with cooling and under an atmosphere of nitrogen to a suspension of 447 milligrams (0.0563 mole) of lithium hydride in 50 milliliters of dry dimethylformamide. After completion of the addition the mixture is allowed to warm to room temperature over a period of about half an hour, then cooled to 0°-5° C., and a solution of 7.8 grams (0.0282 mole) of 2,6-dibromophenyl isocyanate in 25 milliliters of dry dimethylformamide is added dropwise over a two hour period while maintaining the cooled temperature range. The mixture is then allowed to warm to room temperature and stirred overnight under nitrogen to obtain the desired N-(2,6-dibromophenyl)-N'-(2-imidazolidinylidene)urea product in the reaction mixture. The product is recovered from the reaction mixture by pouring the mixture into 400 milliliters of ice water, acidifying with 10 percent hydrochloric acid to pH below 3, filtering to remove impurities, saturating the filtrate with solid sodium chloride and basifying with potassium carbonate to a pH of 8-9 to precipate the N-(2,6-dibromophenyl)-N'-(2-imidazolidinylidene)urea product as a white solid, m.p. 185°-190° C. (dec.)

The thus obtained base urea product is suspended in 40 milliliters of methanol and methanolic hydrogen chloride added thereto to a pH below 2. Ether is then added to precipitate the N-(2,6-dibromophenyl)-N'-(2-imidazolidinylidene)urea hydrochloride as a white solid, m.p. 200°-202° C. (dec.). After two recrystallizations from methanol/2-propanol/ether, there is obtained a purified product, m.p. 215°–217° C. (dec.) to a new solid, m.p. 255° (dec.)

Anal. Calcd. for $C_{10}H_{10}N_4Br_2O\cdot HCl$: C, 30.14; H, 2.78; N, 14.06. Found: C, 30.12; H, 2.81; N, 14.04.

EXAMPLE V

In a similar manner, the following compounds may be prepared:

N-(2-Chloro-6-methylphenyl)-N'-(2-imidazolidinylidene)urea and its hydrochloride.

N-(2-Bromo-6-methylphenyl)-N'-(2-imidazolidinylidene)urea and its hydrochloride.

N-(2-Bromo-6-ethylphenyl)-N'-(2-imidazolidinylidene)urea and its hydrochloride.

N-(2-Chloro-6-ethylphenyl)-N'-(2-imidazolidinylidene)urea and its hydrochloride.

N-(2-Bromo-6-chlorophenyl)-N'-(2-imidazolidinylidene)urea and its hydrochloride.

N-(2-Fluoro-6-methylphenyl)-N'-(2-imidazolidinylidene)urea and its hydrochloride.

N-(2-Methoxy-6-methylphenyl)-N'-(2-imidazolidinylidene)urea and its hydrochloride.

N-(2-Methyl-6-trifluoromethylphenyl)-N'-(2-imidazolidinylidene)urea and its hydrochloride.

N-(2-Chloro-6-fluorophenyl)-N'-(2-imidazolidinylidene)urea and its hydrochloride.

The following examples illustrate the novel pharmaceutical compositions but are not to be construed as limiting:

EXAMPLE VI 1,000 hard gelatin capsules, each containing 200 milligrams of N-(2,6-dichlorophenyl)-N'-(2-imidazolidinylidene)urea are prepared from the following formulation:

|  | Grams |
| --- | --- |
| N-(2,6-Dichlorophenyl)-N'-(2-imidazolidinylidene)urea | 200 |
| Starch | 250 |
| Lactose | 750 |
| Talc | 250 |
| Calcium stearate | 10 |

A uniform mixture of the ingredients is prepared by blending and employed to fill two-piece hard gelatin capsules. The capsules are suitable to be orally administered to subjects with functional bowel disorders.

EXAMPLE VII

Gelatin capsules are prepared as described in Example VI except that in the formulation, 400 grams of N-(2,6-dibromophenyl)-N'-(2-imidazolidinylidene)urea is employed as active agent providing capsules containing 400 milligrams of N-(2,6-dibromophenyl)-N'-(2-imidazolidinylidene)urea.

EXAMPLE VIII

Gelatin capsules are preapred as described in Example VII except that N-(2-ethyl-6-methyl)-N'-(2-imidazolidinylidene)urea is employed as the active agent.

EXAMPLE IX

Gelatin capsules are prepared as described in Example VII except that N-(2,6-dimethylphenyl)-N'-(2-imidazolidinylidene)urea is employed as the active agent.

EXAMPLE X 1,000 compressed tablets, each containing 500 milligrams of N-(2-Chloro-6-methylphenyl)-N'-(2-imidazolidinylidene)urea are prepared from the following formulation:

|  | Grams |
| --- | --- |
| N-(2-Chloro-6-methylphenyl)-N'-(2-imidazolidinylidene)urea | 500 |
| Starch | 750 |
| Dibasic calcium phosphate hydrous | 5,000 |
| Calcium stearate | 2.5 |

The finely powdered ingredients are mixed well and granulated with 10 percent starch paste. The granulation is dried and compressed into tablets using starch as a disintegrant and calcium stearate as a lubricant.

What is claimed is:

1. A method for relieving the symptoms associated with irritable bowel syndrome which comprises administering to an animal having said syndrome a therapeutically effective amount of a urea compound represented by the formula

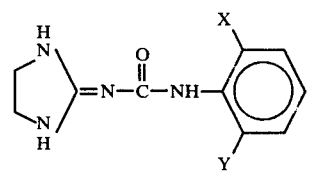

wherein X and Y are selected from methyl, ethyl, chloro and bromo; and pharmaceutically acceptable salts thereof.

2. A method for relieving the symptoms associated with irritable bowel syndrome which comprises administering to an animal having said syndrome from 5 to 500 milligrams per unit dose of a urea compound represented by the formula

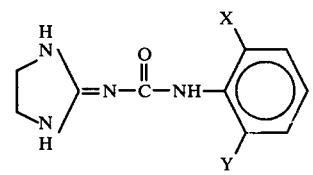

wherein X and Y are selected from methyl, ethyl, chloro, and bromo; and pharmaceutically acceptable salts thereof.

3. A method according to claim 1 in which the urea compound is N-(2,6-dichlorophenyl)-N'-(2-imidazolidinylidene)urea.

4. A method according to claim 1 in which the urea compound is N-(2,6-dimethylphenyl)-N'-(2-imidazolidinylidene)urea.

5. A method according to claim 1 in which the urea compound is N-(2,6-dibromophenyl)-N'-(2-imidazolidinylidene)urea.

6. A method according to claim 1 in which the urea compound is N-(2-chloro-6-methylphenyl)-N'-(2-imidazolidinylidene)urea.

* * * * *

UNITED STATES PATENT AND TRADEMARK OFFICE
CERTIFICATE OF CORRECTION

PATENT NO. : 4,239,768
DATED : DECEMBER 16, 1980
INVENTOR(S) : CHRIS R. RASMUSSEN

It is certified that error appears in the above-identified patent and that said Letters Patent are hereby corrected as shown below:

Claim 3, at Column 10, line 56, "claim 1" should read -- claim 2 --.

Claim 4, at Column 10, line 59, "claim 1" should read -- claim 2 --.

Claim 5, at Column 10, line 62, "claim 1" should read -- claim 2 --.

Claim 6, at Column 10, line 65, "claim 1" should read -- claim 2 --.

Signed and Sealed this

Fourteenth Day of July 1981

[SEAL]

Attest:

Attesting Officer

GERALD J. MOSSINGHOFF

Commissioner of Patents and Trademarks